United States Patent

Rózsa et al.

[11] 4,229,350
[45] Oct. 21, 1980

[54] DIBENZO[d,g][1,3,6]DIOXAZOCINE DERIVATIVES

[75] Inventors: László Rózsa; Lujza Petócz; Katalin Grasser; Ibolya Kosóczky; Enikö Kiszelly; József Nagy, all of Budapest, Hungary

[73] Assignee: Egyt Gyogyszervegyeszeti Gyar, Budapest, Hungary

[21] Appl. No.: 61,042

[22] Filed: Jul. 26, 1979

Related U.S. Application Data

[62] Division of Ser. No. 927,934, Jul. 25, 1978.

[30] Foreign Application Priority Data

Aug. 2, 1977 [HU] Hungary .............................. EE 2515

[51] Int. Cl.² .......................................... C07D 413/06
[52] U.S. Cl. .............................. 260/243.3; 260/244.4
[58] Field of Search .......................... 260/243.3, 244.4

[56] References Cited

PUBLICATIONS

Fischer et al., Chemical Abstracts, vol. 81 (1974) 152203d.

Primary Examiner—Paul M. Coughlan, Jr.
Attorney, Agent, or Firm—Young & Thompson

[57] ABSTRACT

This invention relates to novel dibenzo[d,g][1,3,6]dioxazocine derivatives represented by the general formula I

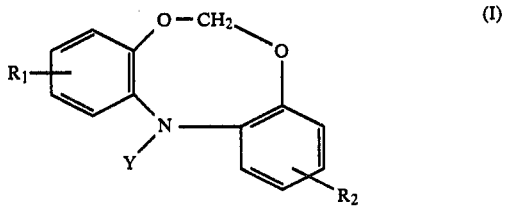

wherein
$R_1$ and $R_2$ independently represent hydrogen, halogen, cyano or trifluoromethyl,
Y stands for hydrogen or a group of formula

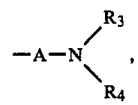

wherein
A stands for a straight or branched chained alkylene having from 2 to 5 carbon atoms and
$R_3$ and $R_4$ independently stand for an alkyl having from 1 to 4 carbon atoms, or
$R_3$ and $R_4$ together with the nitrogen atom they are attached to and optionally together with a further nitrogen atom or with an additional oxygen atom may form a five- or six-membered heterocyclic ring optionally substituted with an alkyl having from 1 to 4 carbon atoms, and pharmaceutically acceptable acid addition salts thereof formed with an inorganic or organic acid.

A process for the preparation of these compounds is also within the scope of this invention.

The above compounds possess valuable pharmaceutical properties, for instance they are effective local anaesthetics and can be used for treating Parkinson syndrome.

3 Claims, No Drawings

DIBENZO[d,g][1,3,6]DIOXAZOCINE DERIVATIVES

This is a division of application Ser. No. 927,934 filed July 25, 1978.

This invention relates to new dibenzoz[d,g][1,3,6]dioxazocine derivatives and to pharmaceutically acceptable, inorganic or organic acid addition salts thereof. The new dibenzo[d,g][1,3,6]dioxazocine derivatives are encompassed by the general formula I

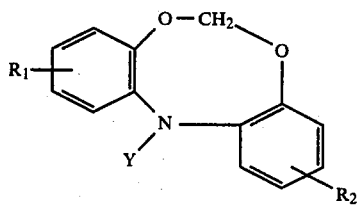

wherein
$R_1$ and $R_2$ independently represent hydrogen, halogen, cyano or trifluoromethyl,
Y stands for hydrogen or a group of formula

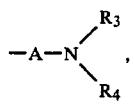

wherein
A stands for a straight or branched chained alkylene having from 2 1 to 5 carbon atoms and
$R_3$ and $R_4$ independently stand for an alkyl having from 1 to 4 I carbon atoms, or
$R_3$ and $R_4$ together with the nitrogen atom they are attached to and optionally together with a further nitrogen atom or with an additional oxygen atom may form a five- or six-membered heterocyclic ring optionally substituted with an alkyl having from 1 to 4 carbon atoms.

A process for the preparation of the compounds having the general formula I, wherein $R_1$, $R_2$ and Y are as defined above, and their inorganic or organic, pharmaceutically acceptable acid addition salts is also within the scope of this invention.

The compounds of the general formula I possess valuable biological activities, for instance they are effective local anaesthetics and can be used for treating Parkinson syndrome.

Also the dibenzo[d,g][1,3,6]dioxazocine structure of the new compounds having the general formula I is new. The structurally closest compounds, i.e. the 5,11-dihydrodibenzo[b,e][1,4]oxazepine and 7,12-dinydro-6H-dibenz[b,e][1,4]oxazocine derivatives are described in the U.S. Pat. No. 3,591,604. These known kompounds show ataractic and antihistamine activity.

In the general formula I Y preferably stands for a group wherein A stands for an ethylene, propylene, or isobutylene group, and $R_3$ and $R_4$ each represent a methyl group. More preferably, $R_3$ and $R_4$ together with the nitrogen atom they are attached to form a pyrrolidine, piperidine or pyridine ring or together with a further nitrogen or with an additional oxygen form a piperazine or morpholine ring.

The most preferred representatives of the pharmaceutically acceptable acid addition salts of the compounds according to the invention are salts formed with hydrochloric acid, hydrobromic acid, sulphuric acid, phosphoric acid, acetic acid, citric acid, oxalic acid, maleic acid, tartaric acid and succinic acid.

The compounds of the general formula I and their pharmaceutically acceptable acid addition salts can be prepared by
(a) for preparing a compound of the general formula III belonging to a narrower group of the compounds having the general formula I

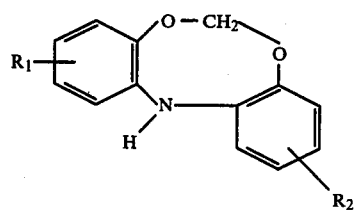

wherein $R_1$ and $R_2$ are as defined above, heating a compound of the general formula II

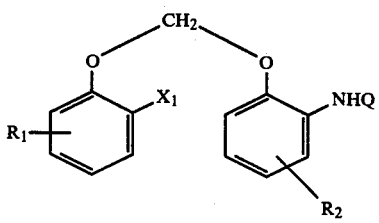

wherein
$R_1$ and $R_2$ are as defined above,
$X_1$ stands for halogen and
Q is hydrogen or formyl,
at 140° to 280° C., preferably at 160° to 240° C., or
(b) for preparing a compound of the general formula III, belonging to a narrower group of the compounds having the general formula I, wherein $R_1$ and $R_2$ are as defined above, reacting a compound of the general formula IV

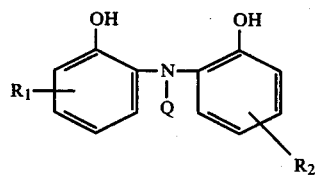

wherein $R_1$, $R_2$ and Q are as defined above, with a dihalomethane of the general formula $$X_2-CH_2-X_3 \qquad (V)$$

wherein $X_2$ and $X_3$ independently represent halogen, and, if desired, aminoalkylating the compound obtained with an aminoalkyl halide of the general formula VI

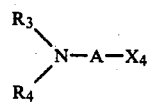

wherein $R_3$ and $R_4$ are as defined above and $X_4$ is halogen, or alkylating the same with a compound of the general formula VII $$X_5—A—X_6 \qquad (VII)$$

wherein $X_5$ and $X_6$ stand for halogen, and aminating the haloalkyl derivative obtained with a compound of the general formula VIII

(VIII)

wherein $R_3$ and $R_4$ have the same meaning as above, and, if desired, converting a compound of the general formula I obtained into an organic or inorganic pharmaceutically acceptable acid addition salt, or converting an acid addition salt into the free base of general formula I.

In the starting compounds of the general formula II in process variant (a) $X_1$ preferably is bromine. The reaction is preferably performed in the presence of a base and a catalyst. As a base for example sodium carbonate, potassium carbonate or butyl-lithium can be used, out of which the use of potassium carbonate proved to be especially advantageous. Suitable catalysts are for instance copper powder, cupric chloride or heavy metal salts.

The temperatures of from 140° to 280° C., preferably from 160° to 240° C., are advantageously achieved in a reaction-inert heat medium the boiling point of which is not lower than the reaction temperature used. For this purpose the eutectic mixture of diphenyl and diphenyl ether is especially advantageous. The commercial name of this medium is Dowtherm$^{(R)}$ A.

The compounds of the general formula II can be prepared according to a method set forth in the U.S. Pat. No. 3,591,604.

In the process variant (b) compounds having the general formula IV are reacted with compounds of the general formula V in the presence of a polar solvent and a base. As a polar solvent both protic and aprotic solvents can be used. The reaction is preferably carried out in the presence of an aliphatic alcohol, e.g. ethanol or N,N-dimethylacetamide. As a base for example sodium metal, sodium hydride or potassium carbonate are generally used.

Compounds having the general formula IV, in which Q stands for hydrogen, can be prepared for example by following the procedure described in publication referred to in Chemical Abstracts, 60, 8022e (1964). The N-formylation of these compounds can be accomplished according to a method described in Beilstein's Handbuck für organische Chemie, Volume 12, p. 235.

The aminoalkylation of a dibenzo[d,g][1,3,6]dioxazocine derivative having the general formula III with a compound having the general formula VI is preferably effected in a polar or apolar solvent, such as xylene or methyl ethyl ketone, in the presence of a base, such as sodium hydroxide or potassium hydroxide.

The aminoalkylation of the compounds having the general formula III can be accomplished also in two reaction steps. In the first step a compound of the general formula III is alkylated with an α,ω-dihaloalkane having the general formula VII, and in the second step the ω-haloalkyl compound obtained is reacted with an amine of the general formula VIII.

The reaction conditions during the reaction of a compound having the general formula III with an α,ω-dihaloalkane of the general formula VII are identical with the reaction conditions described above for aminoalkylation. Amination can be accomplished in the presence or absence of a solvent. Depending on the amine having the general formula VIII the reaction can be carried out under elevated or atmospheric pressure. The reaction temperature preferably is from 80° to 140° C.

The compounds of the general formula I and the inorganic and organic, pharmaceutically acceptable acid addition salts thereof show a prolonged local anaesthetic and antiparkinsonic activity.

Acute toxicity of the compounds was tested on white mice from the strain CFLP. Administration was effected perorally. The $LD_{50}$-values obtained are set forth in the following Table I.

TABLE 1

| Example No. | Acute toxicity $LD_{50}$ (mg./kg.) p.o. |
|---|---|
| 1 | >2000 |
| 3 | 760 |
| 5 | 700 |
| 6 | 270 |
| 7 | 600 |
| 8 | >2000 |
| 15 | 320 |

In order to observe the local anaesthetic activity of the instant compounds 0.25% and 0.5% solution thereof were tested following the method described in Acta Chirurg. Scand. 116, 351 (1958). The test animals were mice.

The concentration at which the activity amounted to 50% ($EC_{50}$) was determined for the test compounds and for Lidocaine (2-diethylamino-2',6'-acetoxy-xylidide) used for comparison. The results obtained are listed in Table II below. In order to make possible a direct comparison of the test compounds with Lidocaine also the $LD_{50}/EC_{50}$-values are given in Table II.

TABLE II

| Example No. | Local anaesthetic activity $EC_{50}$ (%) | $LD_{50}/EC_{50}$ |
|---|---|---|
| 3 | 0.15 | 5060 |
| 5 | 0.32 | 2180 |
| 6 | 0.12 | 2250 |
| 7 | 0.13 | 4600 |
| Lidocaine | 0.18 | 1120 |

From Table II it can clearly be seen that the $LD_{50}/EC_{50}$-value for the compounds according to the invention is 2 to 4.5-times higher than that of Lidocaine.

Since in addition to activity and toxicity also the duration of the activity plays an important role concerning the local anaesthetic activity, the duration of the effect obtained with 0.25% and 0.5% solutions was also observed. The results obtained are listed in Table III below.

TABLE III

| Duration of the local anaesthetic effect | | |
|---|---|---|
| Example No. | Concentration | Duration of the effect (min.) |
| 3 | 0.25 | 71 |
|   | 0.5 | 103 |

TABLE III-continued

| | Duration of the local anaesthetic effect | |
|---|---|---|
| Example No. | Concentration | Duration of the effect (min.) |
| 5 | 0.25 | 34 |
| | 0.5 | 65 |
| 6 | 0.25 | 67 |
| | 0.5 | 161 |
| 7 | 0.25 | 53 |
| | 0.5 | 260 |
| Lidocaine | 0.25 | 25 |
| | 0.5 | 37 |

From the data listed in the above Table III it can be seen that the compounds according to the invention have a much more prolonged activity than Lidocaine, using either of the two concentrations, i.e. they indeed possess a prolonged local anaesthetic activity.

As it has already been stated compounds of the general formula I also exert an antiparkinsonic activity. This activity was tested on white mice, on the basis of the inhibition of tremor induced by tremorine [1,1'-(2-butynylene)-dipyrrolidine] and of nicotine lethality. The results are set forth in the Tables IV and V below. For comparison Trihexyphenidyl [α-cyclohexyl-α-phenyl-1-piperidinepropanol hydrochloride] and L-DOPA [L-(-)-β-(3,4-dihydroxyphenyl)alanine] are used.

TABLE IV

| Inhibition of tremor induced by tremorine (test method: Science, 124, 79 /1956/) | | |
|---|---|---|
| Example No. | $ED_{50}$ (mg./kg.) p.o. | $LD_{50}/ED_{50}$ |
| 3 | 8 | 95 |
| 5 | 18 | 38.9 |
| 6 | 11 | 25 |
| 7 | 30 | 20 |
| 15 | 4.3 | 74.4 |
| Trihexyphenidyl | 15 | 24 |
| L-DOPA | >500 | <5 |

TABLE V

| Inhibition of nicotine lethality (test method: Pharmacodyn., 117, 419 /1958/) | | |
|---|---|---|
| Example No. | $ED_{50}$ (mg./kg.) p.o. | $LD_{50}/ED_{50}$ |
| 3 | 14 | 54 |
| 5 | 60 | 12 |
| 6 | 11 | 25 |
| 8 | 140 | 14 |
| 15 | 9 | 35.6 |
| Trihexyphenidyl | 80 | 4.5 |
| L-DOPA | 500 | <10 |

From the data given in Tables IV and V it appears that the antiparkinsonic activity of the compounds according to the invention surpasses that of the known compounds used for comparison.

The compounds of the general formula I and pharmaceutically acceptable acid addition salts thereof can be converted into pharmaceutical compositions, in a manner known per se, by using conventional carriers and optionally other known additives. Thus, for oral administration tablets, capsules, dragees etc.; injectable solutions, suspensions or emulsions; or aerosol formulations can be prepared. A typical dose for adult patients is 2 to 200 mg./kg.

Further details of the invention are illustrated by the following non-limiting Examples.

EXAMPLE 1

2-Chloro-12H-dibenzo[d,g][1,3,6]dioxazocine

A suspension of 1.4 g. (0.004 moles) of (2-bromophenoxy)-(2-formamido-4-chlorophenoxy)-methane (m.p.: 98° to 100° C.), 0.6 g. (0.0042 moles) of potassium carbonate, 0.2 g. of copper powder and 12 ml. of Dowtherm(®) is heated up to 180° C. and is vigorously stirred at this temperature for 8 hours. The reaction mixture is filtered while hot, then the solvent is evaporated in vacuo. The remaining dark tar is hydrolyzed by boiling in a mixture of 20 ml. of ethanol and 2 ml. of a 20% aqueous sodium hydroxide solution for one hour. The reaction mixture is cooled and neutralized with a 37% aqueous hydrogen chloride solution. The solvent is evaporated and the brown solid residue is extracted with 10 ml. of hot benzene. Thereafter the solvent is eliminated and the residue is crystallized from benzine.

Recrystallization of the crude product from a mixture of 30 ml. of cyclohexane and 2 ml. of xylene affords 0.45 g. (45.6%) of a white product, melting at 182° to 184° C.

Analysis for $C_{13}H_{10}ClNO_2$ (molecular weight: 247.688); Calculated: C 63.05% H 4.07% Cl 14.32% N 5.66%; Found: C 63.46% H 4.29% Cl 14.33% N 5.64%.

EXAMPLE 2

2-Chloro-12H-12-(3-dimethylaminopropyl)-dibenzo[d,g][1,3,6]dioxazocine

A suspension of 1.1 g. (0.0045 moles) of 2-chloro-12H-dibenzo[d,g][1,3,6]dioxazocine and 1.1 g. (0.027 moles) of dry, powdered sodium hydroxide in 20 ml. of xylene is refluxed for three hours in a flask equipped with a water separator, with stirring. Thereafter a solution of 1.62 g. (0.013 moles) of 3-dimethylaminopropyl chloride in 15 ml. of xylene is added in 0.5 hours. The reaction mixture is boiled for 12 hours, cooled to room temperature, then 30 ml. of water are added and the aqueous and organic phases are separated. To the xylene phase a solution of 3.3 g (0.022 moles) of tartaric acid in 25 ml. of water is added and the mixture is stirred for one hour. The aqueous phase is separated and 30 ml. of benzine and 6.4 ml. (0.046 moles) of a 25% aqueous ammonium hydroxide solution are added under vigorous stirring. After separation the benzine phase is dried on ignited magnesium sulphate. The solvent is eliminated. Distillation of the crude product obtained in vacuo affords 1.21 g. (81.8%) of a white crystalline product, melting at 43° to 45° C. Boiling point/0.4 mmHg: 185° to 190° C.

Analysis for $C_{18}H_{21}ClN_2O_2$ (molecular weight: 332.833): Calculated: C 64.96% H 6.36% Cl 10.65% N 8.42%; Found: C 65.78% H 6.66% Cl 10.52% N 8.40%.

EXAMPLE 3

2-Chloro-12H-12-(3-dimethylaminopropyl)-dibenzo[d,g][1,3,6]dioxazocine maleinate To a solution of 1.56 g. (0.0047 moles) of 2-chloro-12H-12-(3-dimethylaminopropyl)-dibenzo/d,g//1,3,6-/dioxazocine in 20 ml. of abs. ether a solution of 0.7 g. (0.06 moles) of maleic acid in 40 ml. of abs. ether is added at 0° C. with stirring. Stirring is continued for one hour, whereupon the precipitated product is filtered off and washed with abs. ether. Recrystallization from isopropanol affords 1.51 g. (71.7%) of a snow-white product, melting at 132° to 135° C.

Analysis for $C_{22}H_{25}ClN_2O_6$ (molecular weight: 448.915): Calculated: C 58.56% H 5.61% Cl 7.90% N 6.24%; Found: C 59.26% H 5.65% Cl 7.89% N 6.17%.

EXAMPLE 4

2-Chloro-12H-12-(2-piperidinoethyl)-dibenzo[d,g][1,3,6]dioxazocine

A suspension of 2.8 g. (0.0113 moles) of 2-chloro-12H-dibenzo[d,g][1,3,6]dioxazocine and 3.1 g. (0.078 moles) of dry powdered sodium hydroxide in 70 ml. of xylene is refluxed in a flask equipped with a water separator for 3 hours, with stirring. Thereafter a solution of 5.0 g. (0.034 moles) of N-(2-chloroethyl)-piperidine in 30 ml. of xylene is added in 0.5 hours and the reaction mixture is stirred for further 12 hours.

Thereafter the reaction mixture is subjected to a treatment described in Example 2. Recrystallization of the product from isopropanol affords 3.44 g. (85.6%) of a white product, melting at 87° to 89° C.

Analysis for $C_{20}H_{23}ClN_2O_2$ (molecular weight: 358.877): Calculated: C 66.94% H 6.46% Cl 9.88% N 7.81; Found: C 66.15% H 7.40% Cl 9.98% N 7.90%.

EXAMPLE 5

2-Chloro-12H-12-(2-piperidinoethyl)-dibenzo[d,g][1,3,6]-dioxazocine hydrochloride A solution of 3.44 g. (0.0096 moles) of 2-chloro-12H-12-(2-piperidinoethyl)-dibenzo[d,g][1,3,6]dioxazocine in 40 ml. of abs. ether is cooled to 0° C. and the pH is adjusted to 2 to 3 by adding a suitable amount of a 15% solution of hydrochloric acid in ether with stirring. The precipitated white crystals are filtered off, suspended in ether and washed.

Recrystallization of the product from isopropanol affords 3.17 g. (83.6%) of a snow-white product, melting at 201° to 203° C.

Analysis: for $C_{20}H_{24}Cl_2N_2O_2$ (molecular weight: 395.342): Calculated: C 60.76% H 6.12% Cl 17.94% N 7.09% Cl⁻ 8.97%; Found: C 59.94% H 5.69% Cl 17.97% N 7.17% Cl⁻ 8.95%.

EXAMPLE 6

2-Chloro-12H-12-(2-methyl-3-dimethylaminopropyl)-dibenzo[d,g][1,3,6]dioxazocine hydrochloride A suspension of 1.44 g. (0.058 moles) of 2-chloro-12H-dibenzo[d,g][1,3,6]dioxazocine and 1.4 g. (0.036 mols) of solid, powdered sodium hydroxide in 30 ml. of xylene is refluxed in a flask equipped with a water separator for 3 hours. To the mixture a solution of 2.46 g. (0.0174 moles) of 2-methyl-3-dimethylaminopropyl chloride in 15 ml. of xylene is added in 0.5 hours and the reaction mixture is boiled for further 12 hours.

The reaction mixture is thereafter subjected to the same treatment as described in Example 2, which results in a white product weighing 1.83 g. (90.6%) and melting at 72° to 75° C. The base is converted into the corresponding hydrochloric acid addition salt according to the procedure described in Example 5.

Recrystallization of the crude product from isopropanol affords 1.63 g. (73.2%) of a white product, melting at 184° to 186° C.

Analysis for $C_{19}H_{24}Cl_2N_2O_2$ (molecular weight: 383.331): Calculated: C 59.53% H 6.31% Cl 18.50% N 7.31%; Cl⁻ 9.25%; Found: C 59.66% H 6.38% Cl 18.57% N 7.35% Cl⁻ 9.23%.

EXAMPLE 7

2-Chloro-12H-12-/2-(N-methylpiperazino)-ethyl]dibenzo[d,g,][1,3,6]dioxazocine dihydrochloride A suspension of 1.24 g. (0.005 moles) of 2-chloro-12H-dibenzo[d,g][1,3,6]dioxazocine and 1.2 g. (0.03 moles) of solid, powdered sodium hydroxide in 20 ml. of xylene is refluxed in a flask equipped with a water separator for 3 hours, with stirring. A solution of 2.44 g. (0.015 moles) of 1-methyl-4-(2-chloroethyl)-piperazine in 20 ml. of xylene is added within 0.5 hours and the mixture is boiled for further 12 hours.

The reaction mixture is thereafter subjected to the same treatment as described in Example 2, which results in a crude base weighing 1.51 g. The crude product cannot be crystallized. The base is converted into the corresponding hydrochloric acid addition salt according to the procedure described in Example 5.

Recrystallization of the crude product from methanol affords 1.61 g. (72.2%) of a snow-white product, melting at 201° to 203° C.

Analysis for $C_{20}H_{26}Cl_3N_3O_2$ (molecular weight: 446.823): Calculated: C 53.76% H 5.87% Cl 23.81% N 9.41%; Found: C 52.55% H 5.80% Cl 23.52% N 9.35%.

EXAMPLE 8

2-Chloro-12H-12-(2-morpholinoethyl)-dibenzo[d,g][1,3,6]dioxazocine maleinate

A suspension of 0.99 g. (0.004 moles) of 2-chloro-12H-dibenzo[d,g][1,3,6]dioxazocine and 0.96 g. (0.024 moles) of solid, powdered sodium hydroxide in 20 ml. of xylene is refluxed in a flask equipped with a water separator for 3 hours, with stirring. To the reaction mixture a solution of 1.79 g. (0.012 moles) of N-(2-chloroethyl) morpholine in 12 ml. of xylene is added in 0.5 hours, whereupon the mixture is boiled for further 12 hours.

Thereafter the reaction mixture is subjected to the same treatment as described in Example 2, which results in a crude base weighing 1.0 g.

The base is converted into the corresponding maleinate salt in the way set forth in Example 3. Recrystallization of the crude product from isopropanol affords 1.04 g. (54.8%) of a snow-white product, melting at 151° to 152° C.

Analysis for $C_{23}H_{25}ClN_2O_7$ (molecular weight: 476.926): Calculated: C 57.92% H 5.28% Cl 7.43% N 5.88%; Found: C 58.19% H 5.45% Cl 7.49% N 5.87%.

EXAMPLE 9

2-Chloro-12H-12-(3-dimethylaminopropyl)-dibenzo[d,g][1,3,6]dioxazocine (A) A suspension of 2.48 g. (0.01 moles) of 2-chloro-12H-dibenzo[d,g][1,3,6]dioxazocine, 6.3 g. (0.04 moles) of 3-chlorobromopropane and 3.2 g. (0.08 moles) of sodium hydroxide in 30 ml. of methyl ethyl ketone is refluxed for 8 hours, with vigorous stirring. A second 3.2 g. portion (0.08 moles) of sodium hydroxide is added to the mixture, which is then refluxed for further 12 hours. The reaction mixture is cooled to room temperature, poured on 30 ml. of ice-water and the organic and aqueous phases are separated from each other. The aqueous phase is extracted with 10 ml. of methyl ethyl ketone. The organic phases are combined, washed with a saturated aqueous sodium chloride solution and dried over magnesium sulphate. Evaporation of the solvent gives a viscous residue, which turns to a crystalline substance spontaneously.

Recrystallization from isopropanol affords 2.0 g. (62.5%) of white 2-chloro-12H-12-(3-chloropropyl)-dibenzo[d,g][1,3,6]dioxazocine, melting at 106° to 108° C.

Analysis for $C_{16}H_{15}Cl_2NO_2$ (molecular weight: 324.218): Calculated: C 59.27% H 4.66% Cl 21.87% N 4.32%; Found: C 59.34% H 4.97% Cl 21.79% N 4.25%.

(B) A solution of 3.24 g. (0.01 moles) of 2-chloro-12H-12-(3-chloropropyl)-dibenzo[d,g][1,3,6]dioxazocine and 4.5 g. (0.10 moles) of dimethyl amine in 30 ml. of benzene is placed into a bumb tube. The equipment is closed, heated up to 100° C. and kept at this temperature for 20 hours. The reaction mixture is then cooled to room temperature, washed three times with 10 ml. portions each of water, the organic phase is separated and the solvent is eliminated. The residue is dissolved in 30 ml. of ether and the solution is extracted with two 20-ml. portions of a 2 N aqueous hydrochloric acid solution. The acid extracts are combined, washed with 10 ml. of ether, whereupon the pH-value is adjusted to 10 with 20% aqueous sodium hydroxide solution. The mixture is eluted with three 10-ml. portions of ether, the combined ethereal extracts are washed with water and dried over magnesium sulphate. The solvent is eliminated and the remaining crude base is purified as described in Example 2 to give 1.34 g. (52.3%) of a pure base. Melting point and analysis data of the product are identical with the corresponding characteristics of the compound obtained in Step A/of this Example.

EXAMPLE 10

2,10-Dichloro-12H-dibenzo[d,g][1,3,6]dioxazocine

A suspension of 4.1 g. (0.01 moles) of (2-bromo-4-chlorophenoxy)-(2-formamido-4-chlorophenoxy)-methane (m.p.: 148° to 149° C.), 2.1 g. (0.015 moles) of potassium carbonate, 0.5 g. (0.008 gatom) of copper powder and 30 ml. of Dowtherm$^{(R)}$ A is heated up to 190° C. and is kept at this temperature for 10 hours, while stirred vigorously. Thereafter the reaction mixture is filtered and from the filtrate the solvent is distilled off in vacuo. The remaining tar is boiled in a mixture of 45 ml. of ethanol and 4.5 ml. of a 20% aqueous sodium hydroxide solution for one hour, then cooled to 20° C. It is then neutralized with a 37% aqueous hydrochloric acid solution and the solvent is eliminated. The residue is extracted three times with 80 ml. portions each of hot cyclohexane, the combined extracts are decoloured while hot and the solvent is eliminated. Recrystallization of the crude product from carbon tetrachloride affords a white product weighing 0.6 g. (21.4%) and melting at 194° to 196° C.

Analysis for $C_{13}H_9Cl_2NO_2$ (molecular weight: 282.137): Calculated: C 55.34% H 3.22% Cl 25.13% N 4.96%; Found: C 55.68% H 3.47% Cl 25.08% N 4.85%.

EXAMPLE 11

2,10-Dichloro-12H-dibenzo[d,g][1,3,6]dioxazocine

To a suspension of 1.17 g. (0.049 moles) of sodium hydride in 40 ml. of N,N-dimethyl acetamide a solution of 6.07 g. (0.02 moles) of 2,2'-dihydroxy-5,5'-dichloro-N-formyl-diphenylamine (m.p.: 180° to 182° C.) is added in one hour, at 25° C., under stirring. The mixture is stirred for a further one hour and 3.55 g. (0.02 moles) of methylene bromide are added to the clear solution in 0.5 hour. The reaction mixture is stirred at 25° C. for 5 hours and subsequently at a water bath for 3 hours. ⅔ of the solvent are eliminated and the residue is cooled to room temperature and poured onto 100 g. of granulated ice. The precipitated solid is filtered off, washed and dried. Recrystallization from carbon tetrachloride affords 3.51 g. (61%) of a white product, melting at 194° to 196° C. The product proved to be identical with the product of Example 10.

EXAMPLE 12

12H-dibenzo[d,g][1,3,6]dioxazocine 1.0 g. (0.044 gatoms) of sodium metal is dissolved in 50 ml. of ethanol. To the solution obtained a solution of 5.0 g. (0.0218 moles) of 2,2'-dihydroxy-N-formyl-diphenylamine (m.p.: 152° to 155° C.) in 50 ml. of ethanol is added. To the clear solution 3.8 g. (0.021 moles) of methylene bromide are added at 25° C., under stirring. The reaction mixture is boiled for 5 hours, whereupon the solvent is eliminated. The remaining tar is extracted with three 30 ml. portions of hot carbon tetrachloride, filtered while hot and the filtrate is concentrated.

Recrystallization of the residue from ethanol affords 1.5 g. (20%) of a white product, melting at 189° to 191° C.

Analysis for $C_{13}H_{11}NO_2$ (molecular weight: 213.24): Calculated: C 73.22% H 5.20% N 6.57%; Found: C 73.36% H 5.41% N 6.44%.

EXAMPLE 13

2,10-Dichloro-12H-dibenzo[d,g][1,3,6]dioxazocine

A mixture of 6.3 g. (0.021 moles) of 2,2'-dihydroxy-5,5'-dichloro-N-formyl-diphenylamine, 3.8 g. (0.022 moles) of dibromomethane, 4.1 g. (0.03 moles) of anhydrous potassium carbonate and 100 ml. of N,N-dimethyl acetamide is heated up to 100° C. and is kept at this temperature for 12 hours under nitrogen, under vigorous stirring.

The reaction mixture is cooled to room temperature and poured on ice. The precipitated product is filtered off, washed with water and subsequently dried. It is then hydrolyzed by boiling with a mixture of 50 ml. of ethanol and 10 ml. of a 20% aqueous sodium hydroxide solution for one hour. Upon cooling the reaction mixture is neutralized with a 37% aqueous hydrochloric acid solution, then the product is precipitated by adding 100 ml. of water, filtered off, washed with water and dried. Repeated recrystallization from carbon tetrachloride affords 3.3 g. (55.6%) of a white product. Melting point and analysis data of the product are identical with those of the product of Example 11.

EXAMPLE 14

2-Chloro-12H-dibenzo[d,g][1,3,6]dioxazocine

A mixture of 6.7 g. (0.025 moles) of 2,2'-dihydroxy-5-chloro-N-formyl-diphenylamine (m.p.: 154° to 157° C.), 4.9 g. (0.03 moles) of dibromomethane, 17.5 g. (0.13 moles) of anhydrous potassium carbonate and 120 ml. of N,N-dimethylacetamide is heated up to 100° C. under nitrogen and kept at this temperature for 12 hours, under vigorous stirring.

The reaction mixture is cooled to room temperature, poured onto ice and the precipitated solid is filtered off, washed with water and dried. Thereafter it is hydrolyzed by boiling in a mixture of 50 ml. of ethanol and 10 ml. of a 20% aqueous sodium hydroxide solution for one hour. The reaction mixture is cooled down, neutralized with a 37% aqueous hydrochloric acid solution and the product is precipitated by adding water to the mixture. The product is filtered off and dried. Recrystallization from isopropanol containing 20% of water affords 4.3 g. (68%) of a white product. Melting point and analysis data of the product obtained are identical with those of the product of Example 1.

EXAMPLE 15

2,10-Dichloro-12H-12-(3-dimethylaminopropyl)-dibenzo[d,g][1,3,6]dioxazocine maleinate A mixture of 11.3 g. (0.04 moles) of 2,10-dichloro-12-H-dibenzo[d,g][1,3,6]dioxazocine, 9.6 g. (0.24 moles) of sodium hydroxide and 450 ml. of xylene is boiled in a flask equipped with a water separator for two hours, with vigorous stirring. Thereafter a solution of 19.4 g. (0.16 moles) of 3-dimethylaminopropyl chloride in 250 ml. of xylene is added to the reaction mixture, followed by the addition of 2.0 g. of potassium iodide, and the mixture is boiled for further 12 hours. The reaction mixture is thereafter subjected to a treatment as described in Example 2 to give 14.0 g. of a crude base which cannot be crystallized.

To a solution of 14.0 g. (0.0382 moles) of a crude base in 150 ml. of abs. ether 4.4 g. (0.0382 moles) of maleic acid in 320 ml. of abs. ether are added under stirring. The mixture is stirred for one hour and thereafter the precipitated product is washed with abs. ether. Recrystallization from acetonitrile affords 13.4 g. (69.5%) of a snow-white product, melting at 190° to 193° C. (decomposition).

Analysis for $C_{22}H_{24}Cl_2N_2O_6$ (molecular weight: 483.364): Calculated: C 54.67% H 5.01% Cl 14.67% N 5.80%; Found: C 54.82% H 4.96% Cl 14.54% N 5.70%.

What we claim is:

1. Compounds of the general formula I

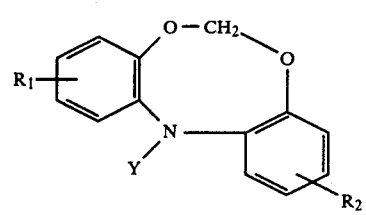

wherein
  $R_1$ and $R_2$ independently represent hydrogen or halogen, and
  Y stands for a group of formula

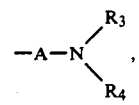

wherein
  A stands for a straight or branched chained alkylene having from 2 to 5 carbon atoms and
  $R_3$ and $R_4$ together with the adjacent nitrogen atom form a piperidino or a piperazino group, wherein the heterocyclic ring may have a $C_{1-4}$ alkyl substituent,
and pharmaceutically acceptable acid addition salts thereof formed with an inorganic or organic acid.

2. A compound as claimed in claim 1, which is 2-chloro-12H-12-(2-piperidinoethyl)-dibenzo[d,g][1,3,6]-dioxazocine and pharmaceutically acceptable acid addition salts thereof.

3. A compound as claimed in claim 1, which is 2-chloro-12H-12-[2-(N-methylpiperazino)-ethyl)]-dibenzo[d,g][1,3,6]dioxazocine-dihydrochloride and pharmaceutically acceptable acid addition salts thereof.